(12) United States Patent  (10) Patent No.: US 9,084,555 B2
 Lautenschläger  (45) Date of Patent: Jul. 21, 2015

(54) METHOD AND APPARATUS FOR DETERMINING THE VASCULARITY OF AN OBJECT LOCATED IN A BODY

(75) Inventor: Stefan Lautenschläger, Hausen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 493 days.

(21) Appl. No.: 13/029,194

(22) Filed: Feb. 17, 2011

(65) Prior Publication Data

US 2011/0201925 A1 Aug. 18, 2011

(30) Foreign Application Priority Data

Feb. 17, 2010 (DE) .......................... 10 2010 008 243

(51) Int. Cl.
 *A61B 5/05* (2006.01)
 *G06K 9/00* (2006.01)
 *A61B 5/055* (2006.01)
 *A61B 5/06* (2006.01)
 (Continued)

(52) U.S. Cl.
 CPC . *A61B 5/055* (2013.01); *A61B 5/06* (2013.01); *A61B 5/489* (2013.01); *A61B 6/481* (2013.01); *A61B 6/504* (2013.01); *G06T 7/0012* (2013.01); *A61B 6/03* (2013.01); *A61B 2019/504* (2013.01); *A61B 2019/524* (2013.01); *G06T 2207/10072* (2013.01); *G06T 2207/20036* (2013.01); *G06T 2207/30056* (2013.01); *G06T 2207/30101* (2013.01)

(58) Field of Classification Search
 CPC .................. A61B 2019/504; A61B 2019/524; A61B 5/055; A61B 5/06; A61B 5/489; A61B 6/03; A61B 6/481; A61B 6/504; G06T 2207/10072; G06T 2207/20036; G06T 2207/30056; G06T 2207/30101; G06T 7/0012
 USPC .......... 600/407, 425; 382/128, 256–257, 130, 382/282, 173
 See application file for complete search history.

(56) References Cited

U.S. PATENT DOCUMENTS 6,058,218 A * 5/2000 Cline ............................ 382/254
7,940,977 B2 * 5/2011 Begelman et al. ............ 382/133
(Continued)

FOREIGN PATENT DOCUMENTS

WO WO 2009/088963 A2 7/2009

OTHER PUBLICATIONS

Moody et al., "Quantification of Afferent Vessels Shows Reduced Brain Vascular Density in Subjects with Leukoaraiosis", Radiology, Dec. 2004, pp. 883-890.*

(Continued)

*Primary Examiner* — Katherine Fernandez

(57) ABSTRACT

A method for determining a vascularity of an object located in a body is proposed. A multidimensional volume image of a target area of the body including the object is acquired. The object is segmented in the volume image. An expanded volume of the object is calculated by expanding structure edges of a volume of the object in the volume image with a predetermined size. The volume of the object is subtracted from the expanded volume of the object for determining an immediate vicinity of the object. A further object in the volume image having a determined minimum volume in the immediate vicinity of the object is segmented. A number of voxels of the further object is compared with a total number of voxels in the immediate vicinity of the object for determining the vascularity of the object.

2 Claims, 1 Drawing Sheet

(51) Int. Cl.
*A61B 5/00* (2006.01)
*A61B 6/00* (2006.01)
*G06T 7/00* (2006.01)
*A61B 6/03* (2006.01)
*A61B 19/00* (2006.01)

(56) References Cited

U.S. PATENT DOCUMENTS

2004/0105527 A1 6/2004 Ferrant et al.
2009/0129673 A1 5/2009 Simon et al.
2009/0221999 A1 9/2009 Shahidi
2009/0252395 A1 10/2009 Chan et al.
2011/0103657 A1* 5/2011 Kang et al. .................... 382/128

OTHER PUBLICATIONS

Xu et al., "A novel method for blood vessel detection from retinal images", Feb. 28, 2010, Biomed Eng Online, vol. 9, pp. 1-10.*

* cited by examiner

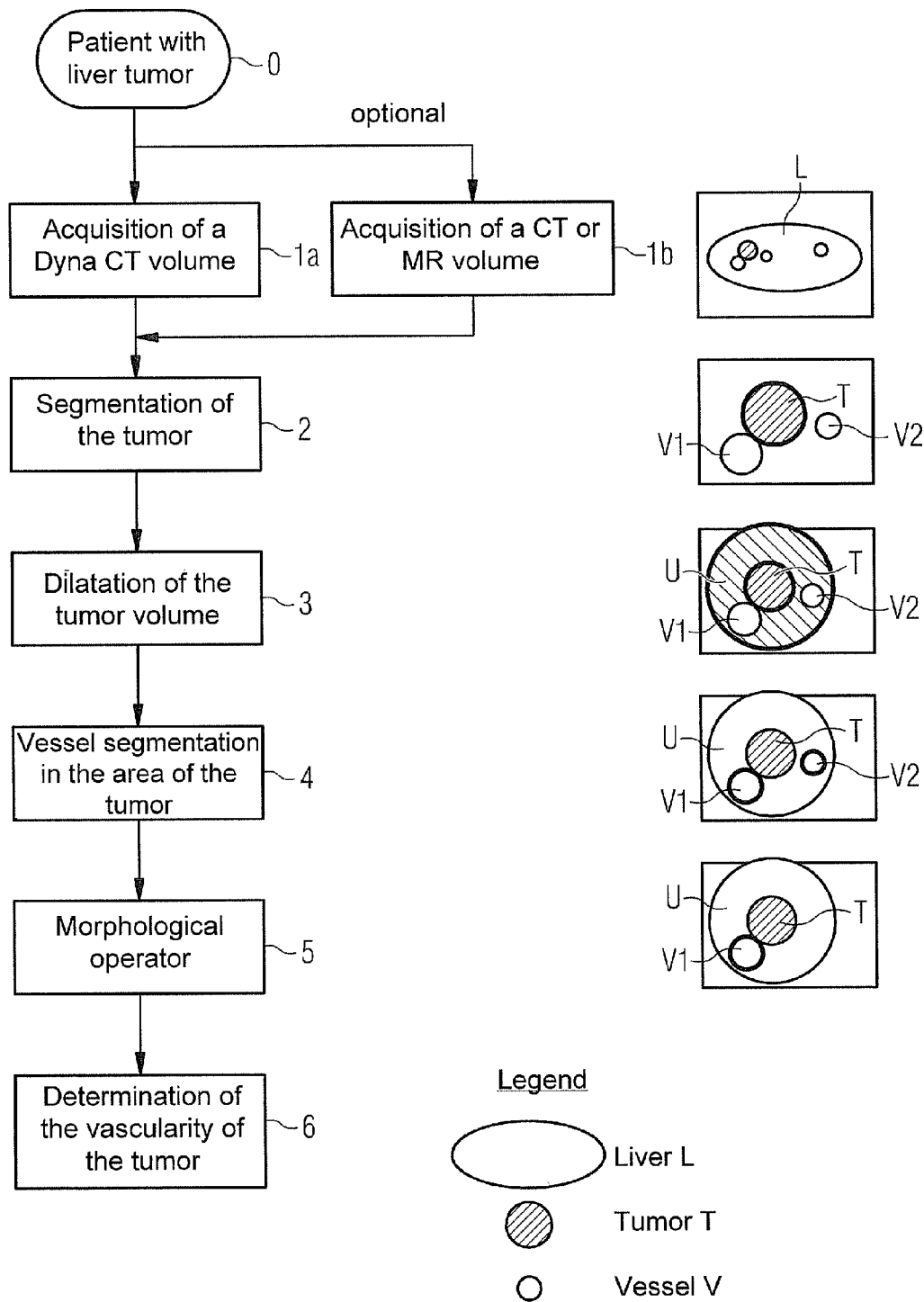

METHOD AND APPARATUS FOR DETERMINING THE VASCULARITY OF AN OBJECT LOCATED IN A BODY

CROSS REFERENCE TO RELATED APPLICATIONS

This application claims priority of German application No. 10 2010 008 243.0 filed Feb. 17, 2010, which is incorporated by reference herein in its entirety.

FIELD OF THE INVENTION

The invention lies preferably in the field of optimized planning for ablation interventions on liver tumors. Such ablation planning is also conceivable for kidneys, lungs and other organs.

BACKGROUND OF THE INVENTION

In the case of liver tumors (or also in the case of HCC=hepatocellular carcinoma or corresponding metastases) ablation therapy is a form of treatment which is becoming increasingly important in the medical field, especially for small cell liver tumors. The reason for this is firstly the interventional nature of this type of action (in contrast to resection, the complication rate is significantly lower, among other things) and secondly the improved mortality tables. This means that ablation therapy exhibits significant advantages compared to resection of the liver. The result of the ablation therapy mainly depends on two factors:

1. Size of the Liver Tumor/Metastasis:

If the longitudinal axis (longest axis of the tumor ellipsoid) is less than $x_{max}$ ($X_{max}$ typically at approx. 3 cm), optimal conditions obtain for ablation therapy using RF (radio frequency). This size is typically measured on the basis of volume data from imaging modalities (e.g. CT, MR, rotational angiography). The stipulated limit of approx. 3 cm applies for RF ablations; microwave ablations or ablations using electroperforations are potentially also able to treat somewhat larger tumors/metastases successfully.

It should be added here that that it does not always make sense to make the limit of the tumors which are treated using ablation therapy dependent on the longest axis of the tumor ellipsoid. It would be advantageous to determine the true volume (in $mm^3$) of the tumor.

2. Vascularity of the Tumor/Metastasis:

RF ablation works with heat. In other words, one (or more than one) needle is inserted into the tumor tissue, and the surrounding tissue is in practice "cooked" (heated until the cells die) by applying a high frequency. In order to "cook" the cells, a minimum temperature must be reached. Depending on the distance of the RF point different cell temperatures are reached; in other words, the further a cell is from the ablation point hotspot (point of maximum heat), the lower the probability that enough energy is yet available at this point (in the form of temperature) to "cook" this cell. It is clear from this explanation that only tumors up to a particular maximum size can be treated using RF ablation. If there are vessels in the immediate vicinity of the tumor to be ablated (e.g. main branches of the liver arteries), these vessels—if they are of a certain minimum size—have a cooling effect. This "vessel cooling" works counter to the desired ablation effect (=heat). In order nevertheless to achieve an ablation effect of the desired size (cf. 3 cm longitudinal axis) these vessels are "eliminated". With smaller, less important vessels this is done by embolization; with larger vessels, which mainly serve to supply the vessels in healthy tissue, this is done by short-time occlusion (e.g. balloon occlusion). The aim with both procedures is to reduce or eliminate the cooling of the tumor tissue, in order to ablate/"cook" a maximally large area.

In the current clinical environment the size of a tumor is determined on the basis of the longitudinal axis methods described above. The vascularity of the tumor is only very rarely examined and taken into account.

This procedure has two major disadvantages:

The longitudinal axis method is thus used because for regular (e.g. spherical) tumors it represents a good approximation for the volume of the tumor. An exact measurement of the volume of the tumor is not really possible, or else is associated with a great deal of manual work for the physician. This means that generally a measurement of the volume is dispensed with. A simple and fast way of measuring the volume of the tumor (in addition to determining the longitudinal axis) would be desirable for the physician, because this would enable him to reach a more accurate decision as to whether the tumor in question can be treated by ablation therapy, or whether a resection is necessary.

Paying little or no attention to the vascularity of the tumor means that the area of the cooked cells is sometimes significantly overestimated. Thus there exists the risk that large parts of the tumor cells are not killed, and the anticipated effect (e.g. the elimination of the entire tumor) is not achieved. Thus there exists the risk of subjecting the patient to an intervention without the anticipated and desired benefit.

A simple and fast statement about the vascularity of the tumor would be desirable for the physician because it would then be possible for him (if necessary) to occlude or embolize the corresponding vessels beforehand, and thus ensure the success of the therapy.

SUMMARY OF THE INVENTION

The object of the invention disclosure is thus to make available a method which enables both the aforementioned parameters to be determined. Expediently the data obtained should be used to enable corresponding next steps to be derived therefrom.

The object is achieved with the method and the apparatus as claimed in the independent claims.

One aspect of the invention is a method for determining the vascularity of an object located in a body, having the following steps:

a) Acquisition of at least one multidimensional volume image of a target area of the body, said image including the object (Step 1), b) Segmentation of the object (Step 2), c) Determination of the immediate vicinity (U) of the object by extending the structure edges of the object by a predetermined size and then subtracting the original object volume from the extended object volume (Step 3), d) Segmentation of further objects with a determinable minimum volume in the immediate vicinity of the object (Step 4 and 5) and e) Determination of the vascularity of the object, the number of voxels of the remaining further objects with the determined minimum volume being compared to the total number of voxels in the immediate vicinity of the object (Step 6).

A further aspect of the invention is an apparatus for determining the vascularity of an object located in a body, having the following means:

a) Means for acquiring at least one multidimensional volume image of a target area of the body, said image including the object, b) Means for segmenting the object, c) Means for determining the immediate vicinity of the object by extending the structure edges of the object by a predetermined size and then subtracting the original object volume from the extended object volume, d) Means for segmenting further objects with a determinable minimum volume in the immediate vicinity of the object and e) Means for determining the vascularity of the object, the number of voxels of the remaining further objects with the determined minimum volume being compared to the total number of voxels in the immediate vicinity of the object.

The advantages of the inventive procedure are:

a) The physician can make an optimal prediction of the success of the upcoming ablation therapy.

b) The parameters are automatically calculated and displayed, resulting in a great simplification of the workflow.

c) An unnecessary intervention for each ablation is avoided, since the physician knows all prerequisites for being able to estimate the success beforehand. As a result the number of unnecessary interventions falls, which is firstly to the good of the patient, and secondly raises the success rate of the service provider.

d) All parameters which enable a decision to be taken as to whether or not an embolization/occlusion is necessary are made available to the physician. In other words, only embolizations/occulusions that are still necessary are performed, which results in savings of time and money.

Advantageous embodiments of the method and of the apparatus are the subject matter of the dependent claims or can be taken from the following description and the exemplary embodiments.

BRIEF DESCRIPTION OF THE DRAWINGS

Further advantages, details and developments of the invention emerge from the following description of exemplary embodiments in conjunction with the drawings.

The FIGURE shows a flow chart of the inventive procedure and diagrammatically a figurative representation of liver L, tumor T, vessels V1, V2 in an environment U.

DETAILED DESCRIPTION OF THE INVENTION

The following workflow with the following steps is inventively proposed:

Step 0: A patient with a tumor T in the liver L is examined.

Step 1a) Acquisition of a DynaCT volume (3D rotational angiography):

A DynaCT 3D volume is acquired, in which the object (preferably filled with contrast agent), in particular a tumor T, in the target area L (preferably liver), as well as other objects, in this example the afferent vessels e.g. V1, V2, are contained.

Step 1b) Optional: Acquisition of a CT or MR Volume:

As an alternative to the DynaCT volume a CT or MR volume can also be acquired, in which tumor and afferent vessels are represented.

Step 2. Segmentation of the tumor:

The tumor T is segmented using current image processing technology. If the tumor is segmented, the following parameters are known:

a) Longest axis of the tumor (cf. "3 cm limit"—as explained above)

b) Tumor volume

With these values the first part for assessing the possible result of the ablation is already known.

Step 3. Dilatation of the tumor volume:

To be able to assess the vascularity of the tumor, vessels V1, V2 are searched for in the immediate vicinity U of the tumor. To be able to extract this "immediate vicinity", the tumor volume is dilatated by the factor $X_o$. The dilatation is what is known as a morphological operation, which expands the edges of a known structure (in this case the tumor) by a determined size ($x_o$) (cf. outer line of U in the diagram). The advantage of dilatation compared to an envelope is that the structure of the tumor is retained; in other words, the method can also produce an ideal result in the case of non-spherical tumors. After the dilatation the original tumor volume is subtracted from the dilatated volume. The result of this is an $x_o$-wide edge area/edge volume around the tumor.

Step 4. Vessel segmentation in the area of the tumor

In an advantageous embodiment, a threshold value method can be used for vessel segmentation in the area of the tumor. Within the surrounding volume U voxels which have a grayscale value above a threshold to be set are then deteitnined. This method is used to detect those voxels which are part of a vessel; in other words, the vessels V1, V2 are segmented within the edge area of the tumor.

Step 5. Deployment of a morphological operator:

It is possible that only vessels of a particular size generate a cooling effect, and thus influence the size of the ablation area. In this step use of the morphological "opening operator" can ensure that only vessels of a particular, adjustable size are taken into account for the further steps. Procedures other than the opening operator are also conceivable. As a result of this step, only vessels of a particular minimum size are still found in the surrounding volume of the tumor.

Step 6. Determination of the vascularity of the tumor:

To be able to determine the vascularity of the tumor, the number of vessel voxels remaining (after performance of step 5) is compared to the total number of voxels within the surrounding volume of the tumor. In accordance with this comparison, a meaningful statement about the vascularity of the tumor can be made. In an advantageous embodiment the distance of each individual vessel voxel can be included with a weighting factor in the summation of the vessel voxels in accordance with its minimum distance from the tumor volume; thus vessels which are spatially closer to the tumor volume are taken more account of in the calculation (and thus in the statement about vascularity) than those voxels which are at a greater distance from the tumor.

In a further embodiment the aforementioned comparison can be presented in the form of a traffic light (e.g. red: high vascularity, amber: medium vascularity, green: lower vascularity).

Once these steps have been performed all parameters (size and vascularity of the tumor) are known, and it is possible for the physician to make a sound prediction of the success of the subsequent ablation therapy.

If the calculated parameters show that ablation therapy has only an insufficient prospect of success in the current situation, the physician has various options: one possible alternative course of action for the physician is the prior embolization/occlusion of the vessels, in order to eliminate their cooling potential. Another option is to dispense with ablation therapy, and to initiate a resection process.

A further aspect of the invention can be an apparatus with means for determining the vascularity of an object T located in a body. Such an apparatus can for example be integrated into a workstation, preferably equipped with one or more display devices, whereby the workstation can be connected to a CT, DynaCT or MR system. The parameters calculated as a result of the inventive method can then be displayed on one or more display devices, for example in the manner described above.

The invention claimed is:

1. A method for determining a vascularity of an object located in a body in order to predict a performance of a subsequent ablation therapy, comprising:
    acquiring a multidimensional volume image of a target area of the body comprising the object;
    segmenting the object in the volume image;
    calculating an expanded volume image of the object by expanding structure edges of a volume of the object in the volume image with a predetermined size;
    subtracting the volume of the object from the expanded volume image of the object for determining an immediate vicinity volume image of the object;
    segmenting vessels within the immediate vicinity volume image of the object having a grayscale value above a threshold;
    identifying vessels from the segmented vessels having a size greater than a particular minimum size wherein only the identified vessels having the size greater than the particular minimum size is remains in the immediate vicinity volume image of the object;
    determining a number of voxels corresponding to the identified vessels in the immediate vicinity volume image; and
    comparing, using a computer, the number of voxels of the identified vessels with a total number of voxels in the immediate vicinity volume image of the object for determining the vascularity of the object; and
    visually displaying the determined vascularity of the object on a display device,
    wherein distances of the voxels of the identified vessels from the object are used as weighting factors in the determination of the vascularity of the object, and
    wherein the voxels that are at a closer distance to the object are taken more into account in the determination of the vascularity than the voxels that are at a greater distance from the object, and
    wherein said visual display of the determined vascularity is used to predict the performance of subsequent ablation therapy.

2. The method as claimed in claim 1, wherein the determined vascularity of the object is visually displayed using different color gradations or grayscale levels.

* * * * *